(12) United States Patent
Reiner et al.

(10) Patent No.: US 8,163,714 B2
(45) Date of Patent: Apr. 24, 2012

(54) INJECTABLE CROSSLINKED AND UNCROSSLINKED ALGINATES AND THE USE THEREOF IN MEDICINE AND IN COSMETIC SURGERY

(75) Inventors: Roland Reiner, Darmstadt (DE); Peter Geigle, Alzenau (DE); Herma Glöckner, Kleinwallstadt (DE); Frank Thürmer, Alzenau (DE)

(73) Assignee: Cellmed AG, Alzenau (DE)

( * ) Notice: Subject to any disclaimer, the term of this patent is extended or adjusted under 35 U.S.C. 154(b) by 0 days.

(21) Appl. No.: 10/599,980

(22) PCT Filed: Mar. 2, 2005

(86) PCT No.: PCT/EP2005/002201
§ 371 (c)(1),
(2), (4) Date: Apr. 3, 2007

(87) PCT Pub. No.: WO2005/105167
PCT Pub. Date: Nov. 10, 2005

(65) Prior Publication Data
US 2007/0179117 A1 Aug. 2, 2007

(30) Foreign Application Priority Data
Apr. 16, 2004 (DE) .......................... 10 2004 019 241

(51) Int. Cl.
*A61K 31/729* (2006.01)
*A61K 8/73* (2006.01)
(52) U.S. Cl. ....................................... 514/54; 424/70.13
(58) Field of Classification Search .................... 514/54; 424/70.13, 70.3
See application file for complete search history.

(56) References Cited

U.S. PATENT DOCUMENTS

| | | | |
|---|---|---|---|
| 4,352,883 A | 10/1982 | Lim | |
| 4,424,208 A | 1/1984 | Wallace et al. | |
| 4,663,286 A | 5/1987 | Tsang et al. | |
| 4,806,355 A | 2/1989 | Goosen et al. | |
| 5,086,350 A | 2/1992 | Nishihata | |
| 5,318,780 A | 6/1994 | Viegas et al. | |
| 5,633,001 A | 5/1997 | Agerup | |
| 5,800,829 A | 9/1998 | Dionne et al. | |
| 5,916,790 A | 6/1999 | Enevold | |
| 5,922,025 A | 7/1999 | Hubbard | |
| 6,214,331 B1 | 4/2001 | Vanderhoff et al. | |
| 6,264,113 B1 | 7/2001 | Dingler | |
| 6,605,294 B2 | 8/2003 | Sawhney | |
| 6,642,363 B1 | 11/2003 | Mooney et al. | |
| 7,955,789 B2 | 6/2011 | Izumi et al. | |
| 2002/0022016 A1 | 2/2002 | Walsh et al. | |
| 2002/0151466 A1 | 10/2002 | Hubbard et al. | |
| 2005/0244358 A1 | 11/2005 | Ochoa | |

FOREIGN PATENT DOCUMENTS

| | | |
|---|---|---|
| EP | 0 727 232 A2 | 8/1996 |
| EP | 1 312 382 A1 | 5/2003 |
| WO | 91-09119 A1 | 6/1991 |
| WO | 93-16111 A1 | 8/1993 |
| WO | 94-21299 A1 | 9/1994 |
| WO | 94-25080 A1 | 11/1994 |
| WO | 96-39464 A1 | 12/1996 |
| WO | 98-23226 A1 | 6/1998 |
| WO | 98-52543 A1 | 11/1998 |
| WO | 00-09566 A1 | 2/2000 |
| WO | 02-41928 A1 | 5/2002 |
| WO | 02-076523 A2 | 10/2002 |
| WO | 03-072155 A1 | 9/2003 |
| WO | 03-082359 A1 | 10/2003 |
| WO | 2004-069294 A1 | 8/2004 |
| WO | 2005-105167 A1 | 11/2005 |

OTHER PUBLICATIONS

The Merck Index, 12th Edition, 1996, p. 758.*
Hawley's Chemical Dictionary, 1997, p. 1092.*
Mancini et al, Journal of Food Engineering, 1999, 30, 369-378.*
Kuo et al, Biomaterials 2001, 22, 511-521.*
Grandolfo et al, Calcified Tissue International, 993, 52, 42-48.*
Wong, Alginates in Tissue Engineering, 2003, 238, 77-86, Abstract.*
Atala et al.—Endoscopic Treatment of Vesicoureteral Reflux with a Chondrocyte-Alginate Suspension—Abstract—Journal of Urology Aug. 1994—No. 152 (2 Pt 2)—pp. 641-643—Discussion 644—1 page—NCBI Sequence Viewer—PubMed ID 8021988—National Library of Medicine—USA.
Bent et al.—Treatment of Intrinsic Sphincter Deficiency Using Autologous Ear Chondrocytes as a Bulking Agent—Neurourology and Urodynamics—2001—pp. 157-165—vol. 20—No. 2—Wiley-Liss, Inc.—USA.
Clayton et al.—The Effect of Capsule Composition on the Biocompatibility of Alginate-Poly-1-Lysine Capsules—Journal of Microencapsulation—Apr./Jun. 1991—pp. 221-233—vol. 8—No. 2—Taylor & Francis Ltd—United Kingdom.
Draget et al.—Alginates from Algae—Polysaccharides and Polyamides in the Food Industry. Properties, Prodyction, and Patents—2005—pp. 1-30—Wiley-VCH Verlag GmbH & Co. KGaA—Weinheim—Germany.

(Continued)

*Primary Examiner* — Shaojia Anna Jiang
*Assistant Examiner* — Ganapathy Krishnan
(74) *Attorney, Agent, or Firm* — Morgan, Lewis & Bockius LLP

(57) ABSTRACT

The invention relates to the use of implantable microcapsules, or microparticles or gels produced from alginates that are crosslinked with bivalent or multivalent cations or that are uncrosslinked, for the treatment of skin defects such as e.g. wrinkles, for the treatment of gastro-oesophageal reflux, urinary incontinence and vesico-ureteral reflux.

20 Claims, No Drawings

OTHER PUBLICATIONS

Ertesvåg et al.—Mannuronan C-5-Epimereses and Their Application for in Vitro and in Vivo Design of New Alginates Useful in Biotechnology—Metabolic Engineering—Jul. 1999—pp. 262-269—vol. 1—No. 3—Academic Press—Available online at http://www.ideallibrary.com—USA.

Jork et al.—Biocompatible Alginate from Freshly Collected Laminaria Pallida for Implanation—Journal of Applied Microbiology and Biotechnology—Feb. 2000—pp. 224-229—vol. 53—No. 2—Springer-Verlag—USA and Germany.

Li et al.—Reexamining the Egg-Box Model in Calcium-Alginate Gels with X-Ray Diffraction—Biomacromolecules—Feb. 2007—pp. 464-468—vol. 8—No. 2—American Chemical Society—USA.

Manojlovic et al.—Immobilization of Cells by Electrostatic Droplet Generation: A Model System for Potential Application in Medicine—Original Research—International Journal of Nanomedicine—2006—pp. 163-171—vol. 1—No. 2—Dove Medical Press Limited—United Kingdom.

Marler et al.—Soft-Tissue Augmentation with Injectable Alginate and Syngeneic Fibroblasts—Plastic and Reconstructive Surgery—Journal of the American Society of Plastic Surgeons—May 2000—pp. 2049-2058—vol. 105—No. 6—USA.

Sperger et al.—Analysis of Composition, Molecular Weight, and Water Content Variations in Sodium Alginate Using Solid-State NMR Spectroscopy—Journal of Pharmaceutical Sciences—Aug. 2011—pp. 3441-3452—vol. 100—No. 8—Published online on Mar. 31, 2011 in Wiley Online Library (wileyonlinelibrary.com) DOI 10.1002/jps.2252—Wiley-Liss, Inc. and the American Pharmacists Association—USA.

Xu et al.—Preparation of the Soft Tissue Bulking Agent Composed of Calcium Alginate Microspheres and Its Resorption in Vito—Chinese Journal of Biomedical Engineering—Oct. 2004—pp. 448-454—vol. 23—No. 5—English Abstract—p. 454—China.

\* cited by examiner

INJECTABLE CROSSLINKED AND UNCROSSLINKED ALGINATES AND THE USE THEREOF IN MEDICINE AND IN COSMETIC SURGERY

This application is a section 371 U.S. National stage application of International Application No. PCT/EP2005/002201, with a international filing date of 2 Mar. 2005, and which claims priority to German Application No. 10 2004 019 241.3, filed Apr. 16, 2004, both of which are incorporated by reference.

1. FIELD OF THE INVENTION

The present invention relates to injectable uncrosslinked and crosslinked alginates and the use thereof in the medical, pharmaceutical and cosmetic surgery field as a filler material for filling up volume and defects. In particular, this invention describes the use of injectable uncrosslinked and crosslinked alginates in the correction of folds and wrinkles by under-injection into the skin, for filling up volume, and the use for treatment of gastro-oesophageal reflux disease, urinary incontinence and vesico-ureteral reflux disease by under-injection into the corresponding sphincter musculature.

2. BACKGROUND OF THE INVENTION

Due to disease- or age-related circumstances or cosmetic requirements, a large demand has arisen in the field of medicine for filling materials in order to assist skin and muscle properties in an advantageous manner by increasing volume.

2.1 Under-injection of Wrinkles

In order to render possible the advantageous treatment of wrinkles, e.g. wrinkles on the face and hands, it is known to inject filler materials, so-called "fillers", into the skin. Wrinkles already develop during childhood due to mimicry and at a later age due to physical damage, such as sun, heat, environment and, at an advanced age, due to typical ageing of the skin. In order to fulfil the wish of many patients for a youthful appearance, various methods for treating wrinkles have been established. Firstly chemical denervation e.g. by botulinum toxin A, secondly levelling of the surface and thirdly treatment with "fillers"—in this case the dermis is lined underneath with endogenous or exogenous substances. The present invention describes the novel use of alginates for use as a "filler" substance. A large number of exogenous fillers, which predominantly consist of biological substances, such as collagen or hyaluronic acid, are available in Europe (e.g.: of collagen: Zyderm®, Zyplast®, Atelocollagen®, Resoplast®. Of Hyaluronic acid: Hylaform®, Restylane®, Perlane®, Juvederm®, Rofilan Hylan Gel®, Hyal-System®, Viscontur®). Collagen is a natural protein which keeps human connective tissue elastic. Preparations for under-injection are obtained from human, porcine and bovine collagen. As is known, it is a disadvantage in this context that humans can react allergically to these protein products and allergy tests must therefore necessarily be conducted before use. It is likewise a disadvantage of collagen preparations that collagen can migrate from the injection site into other areas of skin and cause reddening and swelling there (Millikan, 1989, Long term safety and efficacy with Fibrel in the treatment of cutaneous scars, J Dermatol Surg Oncol, 15:837-842).

Hyaluronic acid is a mucopolysaccharide which occurs in almost every part of a living organism, and in particular in the skin. Hyaluronic acid is formed chemically by straight polymer chains having a molecular weight in the range of from several hundred thousand to millions of Daltons, which contain recurring disaccharide units of N-acetylglucosamine and glucuronic acid linked to one another by glycosidic bonds. A large study has shown that the product Restylane®, which is based on hyaluronic acid, gives significantly better results than the collagen preparation Zyderm® (Narins et al., 2003, A randomized, double-blind, multi-center comparison of the efficacy and tolerability of Restylane versus Zyplast for the correction of nasolabial folds. Dermatol. Surg., 29: 588-95). A disadvantage of hyaluronic acid preparations is that for a visible effect the skin must be treated up to three times at short intervals of time. Swellings may occur here, which subside only after 1-2 days.

Complications two to three years post injectionem—at a time at which the materials injected have long been degraded—are known for both hyaluronic acid preparations and of collagenic acid preparations (Hanke et al., 1991, Abscess formation and local necrosis after treatment with Zyderm or Zyplast Collagen Implant. Journal of American Academy of Dermatology, 25 (no. 2, part 1): 319-26; Moscona et al., 1993, An unusual late reaction to Zyderm 1 injections: A challenge for treatment. Plastic and reconstructive surgery, 92: 331-4).

Liquid silicone has likewise be used for a long time for under-injection of wrinkles. Numerous side effects have adversely emerged here, such as e.g. the formation of nodules, periodically recurring cellulitis and the formation of skin ulcers. Treatment with silicone is therefore no longer regarded as advisable (e.g. Edgerton et al., 1976, Indications for and pitfalls of soft tissue augmentation with liquid silicone, Plast. Reconstr. Surg. 58: 157-65).

2.2 Gastro-oesophageal Reflux Disease

Although gastro-oesophageal reflux disease ("GERD") is a normal physiological phenomenon, it can lead to severe pathophysiological symptoms. Gastro-oesophageal reflux disease describes the reflux of acid, enzymatic liquid from the stomach into the oesophagus. It causes indigestion, belching and vomiting of the gastric acid into the oral cavity or even into the lungs. The consequences of "GERD" are burns in the oesophagus and the formation of ulcers, the normal epithelial tissue being replaced by pathological tissue. In healthy patients, the lower oesophageal sphincter muscle closes after intake of food. In patients suffering from "GERD", this does not happen, instead the muscle relaxes and the gastric acid can flow into the oesophagus on contraction of the stomach. This is the main cause of "GERD"; other causes are possible.

Statistical data demonstrate that approximately 35% of the American population suffers from indigestion at least once a month, and 5 to 10% of these once a day. Medically confirmed endoscopy studies show that 2% of the American population suffers from "GERD". The risk of being affected by this increases from the age of 40 (Nebel et al., 1976, Symptomatic gastroesophageal reflux: incidence and precipitating factors, Am. J. Dig. Dis., 21: 953-6). Endoscopically visible reddening are the first indications of "GERD". An advanced course of the disease can be recognized from destruction of tissue, following by tumorigenesis up to carcinoma (adenocarcinoma of the oesophagus). A diffuse tumorigenesis occurs in 3.5% of patients under the age of 65 and in 20-30% of patients over the age of 65 (Reynolds, 1996, Influence of pathophysiology, severity, and cost on the medical management of gastroesophageal reflux disease. Am J. Health-syst. Pharm 53:5-12).

Attempts to support the sphincter musculature by under-injection of swellable substances, e.g. bovine collagen or Teflon paste, failed because in the course of time the material migrated from the original injection site.

"GERD" is currently in general treated with proton pump inhibitors, with the aid of which the majority of patients can be successfully treated if the dosage is adequate. However, a disadvantage is that because of the high incidence of recurrence after discontinuation of the acid-suppressive therapy, a medicamentous long-term therapy is necessary for a permanent conservative elimination of the symptoms in most patients (Bittinger and Messmann, 2003, Neue endoskopische Therapieverfahren bei gastroösophagealer Refluxkrankheit [New endoscopic therapy methods for gastro-oesophageal reflux disease], Z. Gastroenterol, 41: 921-8). Many patients furthermore are not prepared to take medicaments daily for decades. In addition, there are also the problems of the not inconsiderable cost of such medicamentous long-term therapy.

In addition to open and laparoscopic fundoplication, endoscopic therapy methods have recently been employed, with the aim of addressing the main cause of gastro-oesophageal reflux disease therapeutically, namely the incompetent lower oesophagus sphincter. 3 different basic principles are pursued here, firstly suture techniques (e.g. endoscopic gastroplasty, full wall oplication), secondly radiofrequency application and thirdly injection and implantation methods (e.g. biopolymer injection, implantation therapy). The present invention describes a material for biopolymer injection.

This method is currently carried out with a polymer of ethylene-vinyl alcohol (Enteryx®, Boston Scientific, USA). This is a synthetic polymer which is not biodegradable, is chemically inert, has no antigenic properties and has a permanently spongy-elastic consistency after precipitation in tissue. After dissolving the substance in a solvent (dimethylsulfoxide), it is selectively injected in the liquid state into the oesophagus wall via an endoscopic injection needle under radiological control (support of the musculature, raising of pressure). In the context of a clinical study, it emerged as a disadvantage that in only 60% of the patients more than 50% of the polymer injected was still in situ at the injection site after 6 months, and in some cases even more than 75% of the amount originally injected was no longer detectable (Devière at al., 2002, Endoscopic implantation of a biopolymer in the lower esophageal sphincter for gastro-esophageal reflux: a pilot study. Gastrointes Endsc 2002, 55: 335-41). A migration of the polymers, presumably through the wall into the lumen of the gastrointestinal tract, evidently thus occurs in a considerable proportion of patients in the course of time.

On the basis of the technically comparatively simple method and the results to date, biopolymer therapy seem attractive, although the irreversibility of the method and the migration of the material injected must be regarded critically as disadvantages. The present invention describes a proposed solution to the disadvantages mentioned by the novel use of alginates.

2.3 Urinary Incontinence and Vesico-ureteral Reflux Disease

Urinary incontinence in which an involuntary discharge of urine occurs, can arise as an independent disease or as a concomitant symptom of other diseases. Urinary incontinence, by which over 6 million people are affected in Germany, is often regarded as a taboo subject and is therefore concealed and medical help is scarcely sought. It is therefore difficult to establish precise figures regarding the occurrence of urinary incontinence. Estimates suggest that in Germany about 11% of the over-65s and 30% of the over-80s are affected by urinary incontinence. Among the younger people suffering from incontinence, the proportion of women is predominant. The reason for this is that many women have a weakened musculature of the pelvic floor after pregnancy and childbirth and often too little value is laid on exercising of the pelvic floor after the delivery. At an older age, urinary incontinence often occurs in men as a consequence of benign prostate hyperplasia. In addition to the social pressure of the affliction, patients with urinary incontinence are predisposed towards urinary tract infections, ulcers, rashes and urosepsis. In the USA alone, more than 10 billion US dollars are spent annually on dealing with urinary incontinence.

The causes of urinary incontinence can be diverse, and one cause of this is the muscular weakness of the inner sphincter muscle (m. sphincter urethrae internus) of the bladder musculature. For treatment of urinary incontinence, substances having an anticholinergic action which relax the urinary bladder musculature are extensively administered (e.g. Wein, 1995, Pharmacology of Incontinence, Urol. Clin. North Am., 22: 557-77). The significant side effects of these medicaments are often a disadvantage here.

In addition to medicamentous treatment, surgical methods are employed for therapy of urinary incontinence, e.g. implantation of an artificial sphincter (Lima et al., 1996, Combined use of enterocystoplasty and a new type of artificial sphincter in the treatment of urinary incontinence, J. Urology, 156: 622-4), injection of collagens (Berman et al., 1997, Comparative cost analysis of collagen injection and facia lata sling cystourethropexy for the treatment of type III incontinence in women, J. Urology, 157: 122-4) and polytetrafluoroethylenes (Perez et al., 1996, Submucosal bladder neck injection of bovine dermal collagen for stress urinary incontinence in the pediatric population, Urology, 156: 633-6).

As in the treatment of "GERD", the use of injectable collagens has the adverse effect that the treatment must often be repeated because of migration of the material (Khullar et al., 1996, GAX Collagen in the treatment of urinary incontinence in elderly women: A two year follow up. British J. Obstetrics & Gynaecology, 104: 96-9) and can lead to the occurrence of allergies (McClelland and Delustro, 1996, Evaluation of antibody class in response to bovine collagen treatments in patients with urinary incontinence, J. Urology, 155: 2068-73).

A cause of vesico-ureteral reflux disease is the reflux of urine through the ureter from the bladder in the direction of the kidney during urination. This disease occurs often in young children. The reflux of urine can permanently damage the kidneys by bacterial contamination, from scarring to loss of one or both kidneys. The way to avoid kidney damage must therefore be to avoid kidney infections. This can be effected on the one hand by long-term prophylactic administration of antibiotics with unforeseeable side effects, or on the other hand by surgical correction of the reflux with all the known risks of a surgical intervention.

Although vesico-ureteral reflux in children subsides again by itself in the course of time, in some cases it leads to serious urinary tract and kidney infections up to renal failure. There is therefore the need for a safe, effective, minimally invasive and long-term method for treatment of this reflux disease. The endoscopic treatment method has various advantages over conventional surgical methods: out-patient treatment, no scarring, low risk of postoperative obstruction and lower costs. Various substances have hitherto been proposed for submuscular injection (Teflon®, Polydimethylsiloxan®, Macroplastique®, collagen (bovine), Zyplast®, autologous chondrocytes, fatty tissue and blood). The preparation Deflux® (dextranomer/hyaluronic acid copolymer) has also since been approved by the FDA (Oswald et al., 2002, Prospective comparison and 1-year follow-up of a single endoscopic subureteral polymethylsiloxane versus dextranomer/ hyaluronic acid copolymer injection for treatment of vesicoureteral reflux in children, Urology 2002; 60: 894-7).

Summarizing, it can be said for all the proposed uses that the materials to date for under-injection of polymers have the disadvantage that inflammatory reactions were caused, the materials partially migrated and multiple injections were necessary. These problems are solved in an advantageous manner by the present invention.

3. SUMMARY OF THE INVENTION

The present invention relates to the use of implantable microcapsules or microparticles or gels of alginates crosslinked with di- or polyvalent cations or uncrosslinked alginates for treatment of skin deficiencies, such as e.g. wrinkles, and for treatment of gastro-oesophageal reflux disease, urinary incontinence and vesico-ureteral reflux disease.

Preferably, this invention provides a material for dermal under-injection in the region of the face and hands and for increasing the volume of muscular tissue regions by submuscular lining underneath for treatment of gastro-oesophageal reflux disease, urinary incontinence and vesico-ureteral reflux disease. The material is preferably injected by a needle having a diameter of 18 gauge or less and is degraded neither enzymatically nor by the immune system. The injection can take place via syringes, catheters, needles or other injection or infusion methods. The microparticles, microcapsules or gels used for this invention consist of a biocompatible and non-toxic biopolymer, to which in certain use-forms additives, such as e.g. vitamins, adhesion proteins, antioxidants, antiinflammatory substances, antibiotics, growth factors, hormones, nutrients etc., and also vital cells, can also be added.

The requirements of the filling material for the uses mentioned are:
1. The material should be injectable through a narrow cannula without the geometric shapes, e.g. microcapsules, being destroyed.
2. The preparation of the material must be variable for the various uses such that short- to long-term stabilities can be achieved in vivo.
3. The material should remain at the injection site and not migrate.
4. The material should be dissolvable in an emergency or when the indication has ended.
5. The material must be biocompatible.

These requirements are advantageously achieved by the present invention.

The microparticles, microcapsules and gels mentioned in this invention are advantageously prepared from a hydrophilic and biocompatible biopolymer. The biopolymer mentioned consists of alginates and their derivatives.

Alginate is a naturally occurring anionic unbranched polysaccharide which is isolated from marine brown algae. It is built up from homopolymeric groups of -D-mannuronic acid and -L-guluronic acid, separated by heteropolymeric regions of the two acids. The technical-grade alginates nowadays already obtained in large amounts are employed in industry (e.g. papermaking) and as foodstuffs additive (E number 400-405) (e.g. Askar, 1982, Alginate: Herstellung, Eigenschaften und Verwendung in der Lebensmittelindustrie [Alginates: Preparation, properties and use in the foodstuffs industry]. Alimenta 21: 165-8). However, they are also being employed to an increasing extent in pharmacy, medicine and biotechnology. They are routinely used as a constituent of wound dressings (Gilchrist and Martin, 1983, Wound treatment with Sorbsan—an alginate fibre dressing. Biomaterials 4: 317-20; Agren, 1996, Four alginate dressings in the treatment of partial thickness wounds: A comparative experimental study. Br. J. Plast. Surg. 49: 129-34). Alginates also have been and are being employed in a whole series of "tissue engineering" and "drug delivery" projects (e.g. Uludag et al., 2000, Technology of mammalian cell encapsulation. Advanced Drug Delivery Reviews 42: 29-64). The decisive property of alginates for use in biotechnology and in medicine is their capacity for ionotropic gel formation. The alkali metal salts of alginates are water-soluble, while the salts of alginates with most di- or polyvalent cations form insoluble gels in aqueous solution (so-called hydrogels). The wide range of physical variation of the alginates is determined by a number of factors: viscosity (or molar mass distribution, respectively), concentration, ratio of monomers and affinity of the cation employed for the crosslinking. It is thus known e.g. that alginates crosslinked with calcium form less stable hydrogels than alginates which are crosslinked with barium. Not all alginates are suitable for the use described here, since they can contain impurities which after implantation into humans can cause immune defence reaction, such as, for example, fibrosis or inflammatory reactions (Zimmermann et al., 1992, Production of mitogen-contamination free alginates with variable ratios of mannuronic acid to guluronic acid by free flow electrophoresis, Electrophoresis 13: 269-74).

A highly pure alginate which is preferably to be used can be isolated by using homogeneous algal raw material and standardized processes Jork et al., 2000, Biocompatible alginate from freshly collected Laminaria pallida for implantation, Appl. Microbiol. Biotechnol. 53: 224-229) in accordance with DE OS 198 36 960. The biocompatibility requirements are thereby met.

Purified alginates having an average molar mass of from 20 kDa to 10,000 kDa can be used, and the molar mass is preferably between 100 kDa and 1,200 kDa. The viscosity of a 0.1% strength (w/v) prepared aqueous alginate solution of the alginate to be used can be between 3 and 100 mPa s, and is preferably between 10 and 40 mPa s. The concentration of the alginate for the preparation of the alginate solution to be used is between 0.1 and 4% (w/v), and is preferably between 0.4 and 1% (w/v).

For preparation of the proposed microcapsules, the geometric form thereof is first shaped from the alginate. In order to produce spherical capsules, an alginate solution (e.g. potassium alginate or sodium alginate in physiological saline solution) is expediently formed into drops in a precipitating bath with dissolved crosslinking agent. The crosslinking agent preferably consists of divalent cations, e.g. dissolved calcium or barium (5-100 mM). The precipitating bath additionally preferably also contains a buffer substance (e.g. histidine) and sodium chloride (e.g. 290 mOsmol). Air-charged spray nozzles or other encapsulation and drop formation methods corresponding to the prior art are suitable for the preparation of spherical microcapsules. During the preparation process, additional substances (e.g. vitamins, adhesion proteins, anti-inflammatory substances, antibiotics, growth factors, hormones, nutrients, marker substances, vital cells) can also be introduced into the alginate capsules in the manner known in the prior art. After the preparation, several washing steps with a physiological saline solution or another suitable washing solution and optionally an incubation in a sodium sulfate solution, preferably in accordance with U.S. Pat. No. 6,592, 886, preferably follow. The microcapsules are preferably separated from the precipitating and washing baths with a centrifuge or other suitable methods. Microcapsules of crosslinked alginate are not rigid or solid structures, but are highly flexible and elastic, but nevertheless dimensionally stable.

The size of the microcapsules depends on the drop formation method and on the viscosity (or on the molar mass distribution of the alginate) and the concentration of the alginate solution. Microcapsules having a diameter of from 10 μm to 2,000 μm can be used, capsules having a diameter of from 100 to 400 μm are preferably used. The preparation and transfer to containers of the alginate solution or of the microcapsules of alginate are carried out under sterile conditions and/or the products are subjected to final sterilization using a suitable method corresponding to the prior art (e.g. gamma sterilization). Both the alginate solution and the microcapsules of crosslinked alginate are stable to storage in the frozen state.

Alginates are biopolymers. Their stability in vivo depends on the crosslinking and the concentration. In the present invention, the stability in vivo sought can be controlled via these parameters. For uses which are stable in the long term, barium-crosslinked microcapsules of alginate are preferably used. For less long-term uses, calcium-crosslinked microcapsules of alginate are used. The capsules are preferably suspended in a physiological injectable saline solution or in another injection solution corresponding to the prior art. By the use in capsule form or other insoluble or sparingly soluble geometric forms, diffusion or migration of the material into the surrounding tissue is advantageously prevented. The reason for this property is that they are soft, elastic use forms, whereas hard forms are displaced in the tissue. In order to be able to intensify this effect further, substances which have the effect of histological linkage, after injection, between the alginate capsules or the alginate gel and the surrounding tissue can also be admixed to the alginate or covalently bonded to the alginate. Such substances are known as adhesion proteins (e.g. RGD tripeptides). These substances can advantageously additionally prevent the migration of the alginate use forms injected.

Barium-crosslinked microcapsules of alginate can be dissolved again, if desired, at any point in time after the implantation, e.g. by an injection with an EDTA solution (>1 mM) into the implantation site. Calcium-crosslinked microcapsules can likewise be dissolved with an EDTA solution, but preferably with a citrate solution (>10 mM).

Short-term filling up of volume can be achieved by injection of an uncrosslinked alginate gel, e.g. sodium alginate or potassium alginate dissolved in physiological saline solution. In this context, the viscosity of the uncrosslinked alginate gel is adjusted to the desired aim via the concentration of the alginate. According to the invention, the alginate gel can also be injected simultaneously, e.g. by a parallel injection of the crosslinking agent, e.g. a calcium chloride or barium chloride solution, as a result of which curing of the alginate gel in situ is achieved. Injection of the crosslinking agent for in situ curing can also take place after injection of the alginate gel. Calcium- or barium-crosslinked microcapsules of alginate which are suspended and injected in a non-crosslinked alginate solution can also be used. An excess of crosslinking agent ions, e.g. complexed barium or calcium, which diffuses into the non-crosslinked alginate gel after the implantation and likewise leads to an in situ curing there, can be introduced into the capsules. By addition of complexing agents, so-called "retardants" (e.g. sodium triphosphate), to the uncrosslinked alginate gel directly before injection and simultaneous addition of the crosslinking agent, e.g. in the form of calcium or barium sulfate, a delayed crosslinking of the alginate gel occurs, so that an easy injection of the alginate solution is possible, but crosslinking of the alginate gel to give a stable highly viscous gel starts at the implantation site in the course of time. The same effect of in situ crosslinking can be achieved if D-glucono- -lactone (GDL) and the crosslinking agent in the form of calcium or barium carbonate are added to the uncrosslinked alginate solution directly before the injection. Due to the GDL, a slight acidification of the alginate solution occurs in the course of time, which has the result that the calcium and barium carbonates dissociate into hydrogencarbonates and free calcium or barium and these cations crosslink the alginate in situ.

In a use form on humans, the invention comprises the use of the alginate material for treatment of skin wrinkles by inter- or subdermal under-injection of the areas of skin affected. Preferably, the microparticles, microcapsules or gels of alginate are injected by a syringe having a needle diameter of 26 gauge or less, or other suitable techniques. The injection can be carried out either by multiple or several-fold injection into the areas of skin affected, only a very small volume being transferred at each puncture, until a total volume of from 0.1 ml to 2 ml has been under-injected. A planar cushioning and tightening of the skin is thereby achieved, which leads to disappearance or partial disappearance of the wrinkles in the corresponding area. Alternatively, the injection is carried out one to several times, a large volume being applied, preferably by slow withdrawal of the injection needle with simultaneous under-injection of volume, this injection method being particularly suitable for deeper wrinkles. In one use form, barium-crosslinked microcapsuies of alginate having a diameter of 50-400 μm, preferably having a diameter of 200 μm are injected. According to the invention, other use forms described above can also be used, e.g. injection of calcium-crosslinked microcapsules of alginate or injection of uncrosslinked alginate gels with and without methods for in situ crosslinking. The invention of dermal under-injection with crosslinked and uncrosslinked alginates described here is suitable for skin deficiencies which are caused by e.g. ageing, environmental influences, weight loss, pregnancy, surgical interventions and acne. The use according to the invention is suitable in particular for treatment of forehead wrinkles, anger wrinkles, worry wrinkles, slack eyelids, crows' feet, nasolabial wrinkles and for under-injection of lips and for treatment of wrinkles in the hand region.

In a further use form on humans, the invention comprises treatment of gastro-oesophageal reflux disease by implantation or injection of the microcapsules into the wall regions of the lower oesophageal sphincter muscle. The sphincter volume increases in proportion to the volume of microcapsules injected. As a result, the inner lumen of the sphincter muscle becomes smaller and thus allows better contraction of the muscle and thus prevents discharge of gastric acid into the oesophagus. According to the invention, other use forms described above can also be used, e.g. injection of calcium-crosslinked microcapsules of alginate or injection of uncrosslinked alginate gels with and without methods for in situ crosslinking. The implantation is preferably to be carried out with standard techniques which correspond to the prior art, such as e.g. endoscopic or laparoscopic techniques.

In a further use form on humans, the microcapsules are injected into the ureteral sphincter, the bladder sphincter or the urethral musculature for treatment of urinary incontinence and of vesico-ureteral reflux disease. The sphincter volume increases in proportion to the volume of microcapsules injected. As a result, the inner lumen of the sphincter muscle becomes smaller and thus allows better contraction of the muscle, as a result of which the probability of urinary incontinence decreases. According to the invention, other use forms described above can also be used, e.g. injection of calcium-crosslinked microcapsules of alginate or injection of uncrosslinked alginate gels with and without methods for in situ crosslinking. The implantation is preferably to be carried out using standard techniques which correspond to the prior art, such as e.g. endoscopic or laparoscopic techniques.

The use of crosslinked alginates, e.g. in the form of microcapsules, is also suitable in the case of temporary, non-chronic occurrence of forms of urinary incontinence and of gastro-oesophageal and vesico-ureteral reflux disease, since according to the invention, the crosslinked alginates can be dissolved again by injection of an EDTA or citrate solution or a solution of other complexing agents.

The uses according to the invention for under-injection of wrinkles, for treatment of gastro-oesophageal and vesico-ureteral reflux disease and for treatment of urinary incontinence can be combined with conventional treatment methods.

A summary of the primary advantages of the present invention over the prior art is:
- Minimally invasive interventions on the patient compared with conventional surgical treatment methods
- Longer-lasting effects compared with conventional therapies
- Good tolerability and biocompatibility
- Avoidance of repeated interventions
- Avoidance of migration of material
- High flexibility and elasticity with simultaneous dimensional stability
- High variability of the stability
- Reversibility of the use.

EXAMPLES

1. Preparation of a 0.6% (w/v) Alginate Solution

The 0.6% (w/v) alginate solution is prepared under laminar flow. All the reagents and materials required must be sterile. A sterile 50 ml polystyrene tube is tared. 0.15 g of dried alginate as the solid substance is introduced into the tube with a sterile spatula under laminar flow. 25 ml of 0.9% NaCl solution are added with sterile pipette under laminar flow. The closed tube is rotated (test tube rotating apparatus) until the alginate has dissolved completely. The alginate solution prepared in this way can now be used for preparation of microcapsules of alginate (see Example 3), or it is transferred into syringes in a sterile manner according to the prior art and marketed.

2. Preparation of the Barium-containing Precipitating Bath for Crosslinking of the Microcapsules of Alginate The data relate to the preparation of one liter of precipitating bath.

4.48 g $BaCl_2$, 0.77 g histidine, 7.25 g NaCl and 1,000 ml of sterile distilled water are weighed out or measured out and transferred into a glass beaker. The solution is stirred until all the substances have dissolved. The pH of the solution is then adjusted to pH 7±0.1 with NaOH or HCl. The osmolality of the solution prepared is checked with a freezing point osmometer, and must be 290 mOsmol±3 mOsmol. The solution is then autoclaved and can then be used for the preparation of barium-crosslinked microcapsules of alginate (see Example 3).

3. Preparation of Barium-crosslinked Microcapsules of Alginate

The alginate solution (see Example 1) is first subjected to sterile filtration under laminar flow. This is carried out by filtration through a 0.2 μm sterile filter. The solution is forced slowly through the filter and collected in a sterile 50 ml centrifuge tube. The tube is closed and labelled. The alginate solution is centrifuged at 1,000±100 rpm for 5±1 min at room temperature. The autoclaved encapsulating apparatus is screwed with 2 screws at a height of 10±2 cm to an electrically regulatable syringe advancer. A compressed air hose is connected to the apparatus with a clamp and the compressed air is then regulated to a value of 3±1.0 l/min. An open Petri dish is placed under the drop formation nozzle. Three portions of 1±0.1 ml each of sterile water are flushed through the nozzle channel with a 1 ml syringe for cleaning. The speed of the advancers is adjusted to 3±0.5 units. A sterile 1 ml syringe is filled with the centrifuged alginate solution without air bubbles and fitted on to the nozzle. In order to prepare capsules having a diameter of 200 μm, the diameter of the channel of the drop formation nozzle must be approx. 100 μm. The nozzle advancer is switched on and a new Petri dish with 40 ml of precipitating bath (see Example 2) is placed under the nozzle. Drops of alginate now form at the end of the nozzle which are torn off by the stream of air and fall into the precipitating bath. The encapsulation is carried out until the syringe is empty. The capsules cure in the precipitating bath for 10 minutes. When the alginate capsules have cured, they are transferred into a 50 ml centrifuge tube with 10±1 ml of 0.9% NaCl solution. The capsules are then washed 5 times with 10±0.1 ml of 0.9% NaCl. Thereafter, the capsules are transferred into 10 ml of 6 mM $Na_2SO_4$ solution and placed in an incubator (37° C., 5% $CO_2$) for 20±2 min. Thereafter, the $Na_2SO_4$ solution is stripped off and 10±0.1 ml of 0.9% NaCl solution are added and incubation is carried out in an incubator (37° C., 5% $CO_2$) for 20±2 min. Thereafter, the capsules are washed 5× with 10±1 ml of 0.9% NaCl solution. The capsules are then transferred into a polystyrene tube with physiological saline solution and transferred with a high packing density into disposable injection syringes under sterile conditions in units of 1 ml each and marketed.

The invention claimed is:

1. A method of increasing tissue volume in a subject, said method comprising injecting a composition, said composition comprising microparticles of cross-linked alginate, wherein said microparticles of alginate are fully crosslinked with a divalent or polyvalent cation, wherein said alginate, prior to said crosslinking, has a molecular weight of between about 100 kDa and about 1200 kDa and is present in solution at a concentration of from 0.4% to 1% (w/v), and wherein the injection of the composition increases the tissue volume after injection.

2. The method of claim 1, wherein said tissue is skin.

3. The method of claim 1, wherein said tissue is muscle tissue.

4. The method of claim 3, wherein said muscle tissue is a sphincter muscle.

5. The method of claim 4, wherein the sphincter muscle is the lower esophageal sphincter muscle.

6. The method of claim 4, wherein the sphincter muscle is the inner sphincter muscle of the bladder.

7. The method of claim 1, wherein said composition comprises potassium or sodium alginate.

8. The method of claim 1, wherein said divalent or polyvalent cation is barium.

9. The method of claim 8, wherein said microparticles of alginate are crosslinked with barium and at least one additional cation.

10. The method of claim 9, wherein said at least one additional cation is calcium.

11. The method of claim 1, wherein said divalent or polyvalent cation is calcium.

12. The method of claim 11, wherein said microparticles of alginate are crosslinked with calcium and at least one additional cation.

13. The method of claim 1, wherein said composition further comprises at least one additional compound selected from the group consisting of vitamins, adhesion proteins, anti-inflammatory substances, antibiotics, growth factors, hormones, nutrients, and cells.

14. The method of claim 1 or 8, wherein the composition further comprises a pharmaceutical carrier.

15. The method of claim 1 or 8, wherein the diameter of said microparticles is from about 20 to about 2000 μm.

16. The method of claim 1, further comprising injecting at least one solution selected from the group consisting of a citrate solution and a solution of a complexing agent.

17. The method of claim 1, wherein said composition further comprises a physiological carrier.

18. The method of claim 1, wherein said alginate solution further comprises D-glucono-δ-lactone and at least one compound selected from the group consisting of barium carbonate and calcium carbonate.

19. The method of claim 18, further comprising injecting EDTA or citrate solution after said injection of said alginate composition.

20. The method of claim 16, wherein the solution of a complexing agent comprises EDTA.

* * * * *